US006533787B1

United States Patent
Lenke et al.

(10) Patent No.: US 6,533,787 B1
(45) Date of Patent: Mar. 18, 2003

(54) CONTOURABLE SPINAL STAPLE WITH CENTRALIZED AND UNILATERAL PRONGS

(75) Inventors: Lawrence G. Lenke, St. Louis, MO (US); Joseph W. Tai, Bartlett, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 290 days.

(21) Appl. No.: 09/628,761

(22) Filed: Jul. 31, 2000

(51) Int. Cl.[7] ............................................... A61B 17/56
(52) U.S. Cl. ........................................... 606/61; 606/75
(58) Field of Search ............................. 606/61, 69, 70, 606/71, 151, 75

(56) References Cited

U.S. PATENT DOCUMENTS

| | | | | |
|---|---|---|---|---|
| 4,047,524 A | * | 9/1977 | Hall | 128/69 |
| 4,651,724 A | | 3/1987 | Berentey et al. | |
| 5,108,395 A | * | 4/1992 | Laurain | 606/61 |
| 5,147,361 A | | 9/1992 | Ojima et al. | |
| 5,306,275 A | | 4/1994 | Bryan | |
| 5,487,741 A | * | 1/1996 | Maruyama et al. | 606/60 |
| 5,603,714 A | | 2/1997 | Kaneda et al. | |
| 5,616,144 A | * | 4/1997 | Yapp et al. | 606/61 |
| 5,620,443 A | | 4/1997 | Gertzbein et al. | |
| 5,899,904 A | * | 5/1999 | Errico et al. | 606/61 |

FOREIGN PATENT DOCUMENTS

| | | |
|---|---|---|
| DE | 9217768 | 8/1993 |
| EP | 0615728 | 9/1994 |
| EP | 0820730 | 7/1997 |

OTHER PUBLICATIONS

*Anterior Spinal Fixation After Lumbar Corpectomy*, by Thomas Zdeblick, M.D.; Osamu Shirado, M.D., Paul C. McAfee, M.D., Henry DeGroot, M.D. & Karen E. Warden, © 1991 by the *Journal of Bone and Joint Surgery, Incorporated*.
*Kaneda Anterior Spinal Instrumentation System* and *Kaneda Anterior Spinal Screws*, by AcroMed Corporation, p. B–12.
*Kaneda Anterior Spinal Instrumentation for the Thoracic and Lumbar Spine*, by Kiyoshi Kaneda, pp. 413–422.

* cited by examiner

*Primary Examiner*—Todd E. Manahan
(74) *Attorney, Agent, or Firm*—Woodard, Emhardt, Naughton, Moriarty & McNett LLP

(57) ABSTRACT

A staple for stabilizing the attachment of a vertebral screw and a longitudinal member to the spine. The staple has a plate with first and second apertures. All the staple's legs, prongs, or spikes attached to the underside of the staple are located closer to one particular aperture than the other. Preferably, the plate is also "bow-tie" shaped with a groove that separates the wings of the bow-tie. This bow-tie or hour glass shape combined with the groove help the surgeon to more easily conform the plate to the patient's vertebra.

23 Claims, 5 Drawing Sheets

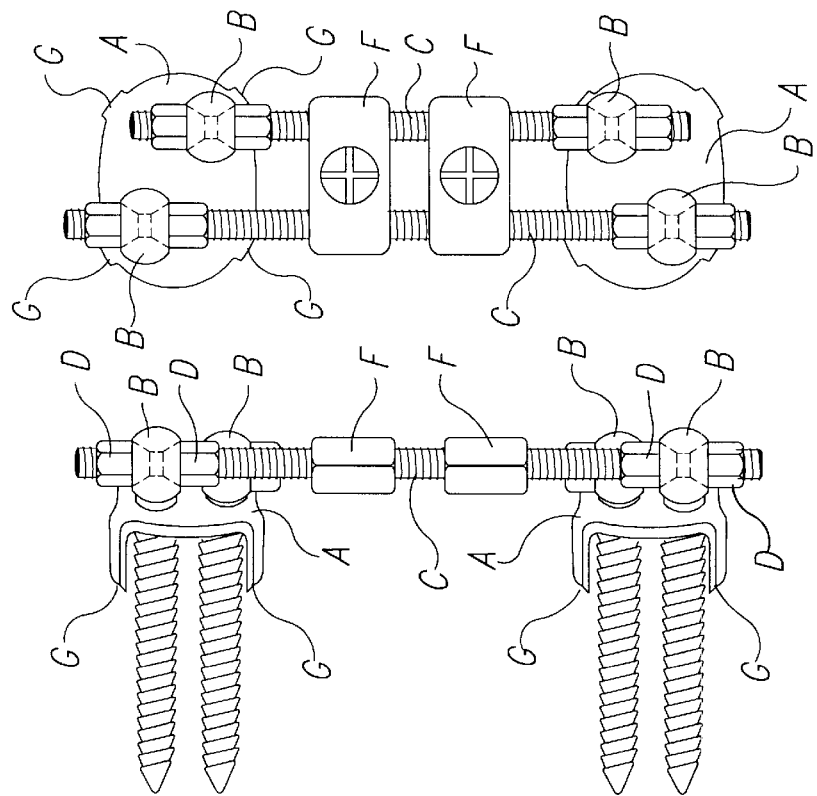
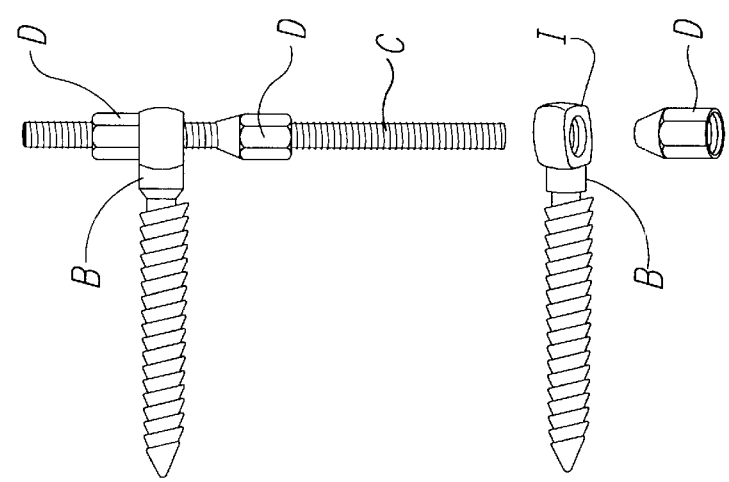
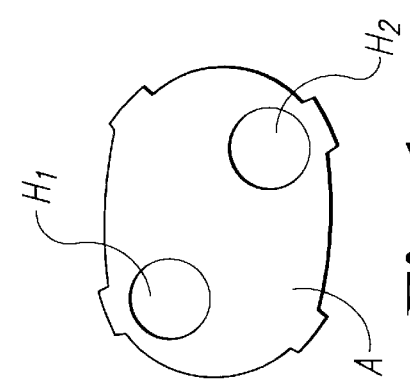

CONTOURABLE SPINAL STAPLE WITH CENTRALIZED AND UNILATERAL PRONGS

BACKGROUND OF THE INVENTION

This invention relates to surgical spinal implant systems, and particularly to those using spinal rods contoured for connection at various locations along the spinal column.

Spinal fractures often occur at the thoracolumbar junction. Most of these fractures are burst injuries, which are particularly dangerous because retropulsed bone fragments can cause spinal cord or caudal equina injuries. Posterior fixation has long been the primary approach for traumatic spinal injuries of this type.

The development of posterior internal fixation procedures for burst fractures was a substantial improvement over early approaches of bed rest and body casts. Several disadvantages to posterior fixation were, however, discovered. For example, this approach fails to reduce kyphosis or allow complete clearing of the spinal canal. Other complications include psuedoarthroses, late rod disengagement and inadequate reduction. Some posterior instrumentations require the fusions to extend at least two levels above and below the injury, particularly at the thoracolumbar junction. The posterior approach is also limited in the viability for use in burst fractures because in such fractures, neural compression generally occurs from the anterior direction. Therefore, it is generally better to decompress and fuse the spine from the anterior.

There are several advantages to anterior internal fixation. An anterior approach allows complete clearance from the spinal canal of bone fragments and for total resection of a tumor. It also permits fusion of a minimal number of motion segments. Yet in spite of these advantages, the use of anterior approaches has been limited by the risk of complications or other disadvantages.

Several plate and screw systems have been designed for anterior instrumentation of the spinal column. The Syracuse I-Plate may use rigid or semi-rigid screws in combination with a plate. But distraction or compression of the bone graft is not possible with this system. The CASF Plate marketed by AcroMed is designed to be used in a semi-rigid manner. This device, as well, does not permit compression or distraction of the bone graft and in addition cannot be used in a rigid construct. The Stafix Plating System marketed by Daruma of Taipei, Taiwan is an anterior thoracolumbar plate designed to address similar indications. This plate incorporates slots and holes as well as permitting quadrilateral placement of screws. The Anterior Thoracolumbar Plating System (Medtronic Sofamor Danek) is a slotted plate designed to attach to the anterior lateral aspect of the vertebral body. The plate allows distract and/or compression through the use of two screws and two bolts.

Several modular spinal instrumentation systems have also been developed for anterior procedures. One such device, the Kaneda device, is shown in FIGS. 1 to 6. As shown, the device extends fixation one vertebral level cephalad and one level caudal to the vertebra in question. A typical construct has two vertebral body staples A, four vertebral screws B, two rods C, eight nuts (one on each side of a screw) and two transverse fixators F. Each vertebral body staple A has four spikes, one on each corner of the staple, to initially secure the staple to a vertebra. Vertebral screws B are then placed through holes H1 and H2 into the cephalad and caudal vertebrae. Rods C are located in the holes I in each screw B with the internal nuts D loosely threaded on each rod. The external nuts, also identified as "D" are then threaded onto the rods. Thereafter, the surgeon tightens all nuts against each side of a screw with the surgeon applying compressive or distractive forces as required. The anterior and posterior rods C are then coupled with transverse fixators F. Specific indications for such modular devices may include deficient anterior bone mass due to trauma, tumor, infection, degenerative disease, congenital causes, or deformity.

The Kaneda system is not entirely satisfactory, largely resulting from the design of vertebral staple A. The staple is used to stabilize screw B much the same way as a washer is used to stabilize a bolt in most any mechanical attachment. These staples, however, are placed on a vertebra, not a uniformly flat surface. Hence, the staple curvature should ideally match the contour of the surface of the vertebra before use. And even if the fit is perfect, it may still be unsatisfactory if the spikes on one end, say the two near hole H1, are pulled from the vertebra when a screw is tightened in the hole on the other end, H2 in our example. This "rocking" effect is depicted in FIG. 7.

Further details regarding staples in a spinal fixation device can be found in Kiyoshi Kaneda, *Kaneda Anterior Spinal Instrumentation for the Thoracic and Lumbar Spine,* Spinal Instrumentation, Williams & Wikins, (Baltimore, Hong Kong, London, Munich, Philadelphia, Sydney, Tokyo), pp. 413 et seq, the disclosure of which is specifically incorporated into this specification by reference.

As a result, there is a need for a vertebral staple in a modular system that can be more easily contoured to the surface of a vertebra, and that does lift spikes on one side of the staple from the vertebra when the other side is tightened. The following is one solution to this need.

SUMMARY OF THE INVENTION

In one aspect, this invention is a vertebral staple with a plate having at least two apertures to receive a spinal bolt, and at least two legs (also identifiable as prongs or spikes) integrally mounted to the bottom of the plate and wherein all legs mounted on the bottom of the plate are closer to one particular aperture for passing a spinal bolt than another aperture for passing a spinal bolt.

In another aspect, this invention is a vertebral staple with a plate having at least two apertures to receive a spinal bolt. The bottom of the plate has at least one leg (also identifiable as a prong or a spike) integrally mounted near the lateral edge of the plate, and at least one leg integrally mounted on the interior of the plate, with all legs mounted on the bottom of the plate closer to one particular aperture for passing a spinal bolt than another aperture for passing a spinal bolt.

In yet another aspect, this invention is a vertebral staple with a plate having a groove therein dividing the plate into a first portion and a second portion. Each of the first and second portions have at least one aperture for passing a bone bolt through the plate and into the vertebra to which the staple is attached. In addition, the bottom of the first portion of the plate has at least two legs (also identifiable as prongs or spikes) integrally attached to the plate, while no legs are mounted on the bottom of the second portion of the plate.

BRIEF DESCRIPTION OF THE DRAWINGS

FIG. 1 is a plan view of a prior art vertebral staple.

FIG. 2 is an exploded view of a prior bone bolt and longitudinal member.

FIGS. 3 and 4 are respectively side and plan views of a prior art spinal fixation system.

DESCRIPTION OF THE PREFERRED EMBODIMENTS

Figure 5:
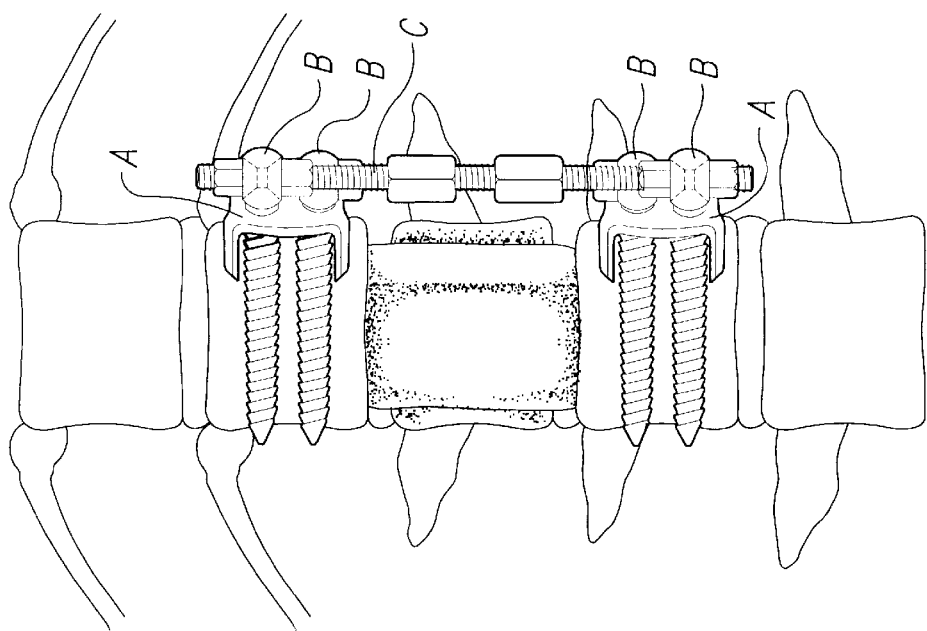
FIGS. 5 and 6 are respectively plan and side views of a prior art spinal fixation system shown attached to the spine.
Figure 6:
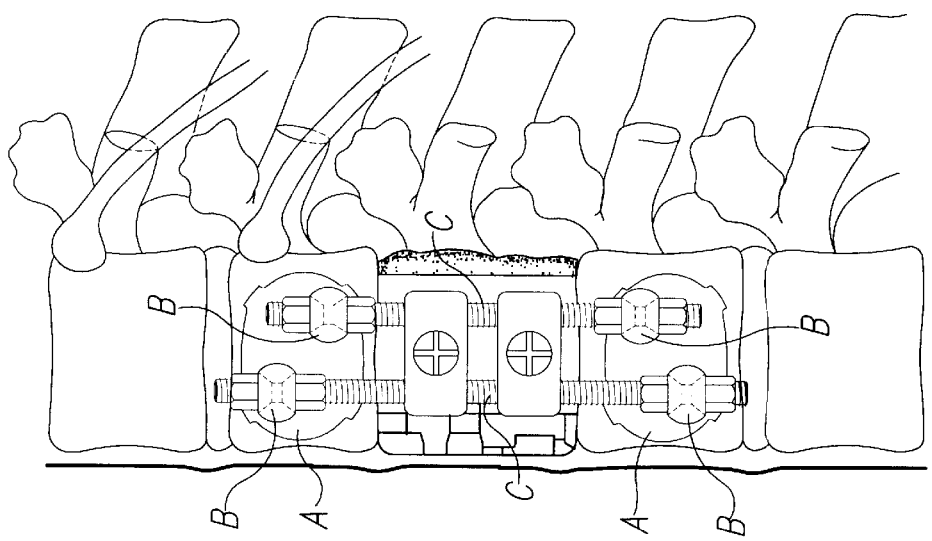
Figure 7:
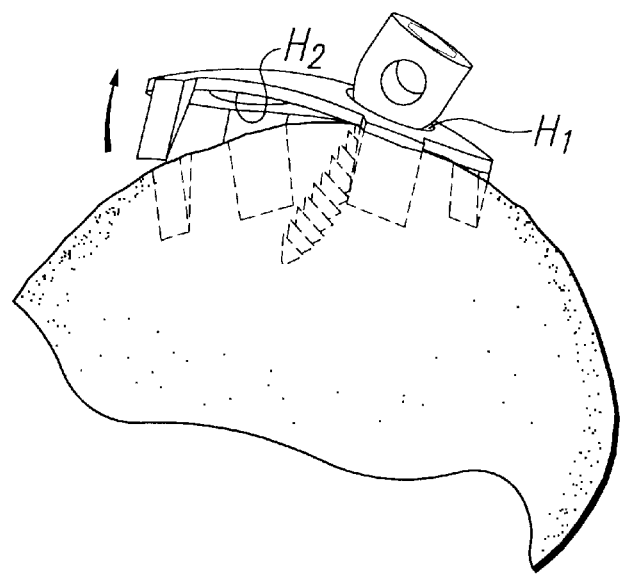
FIG. 7 is a side view of a prior art vertebral staple.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the illustrated invention being contemplated as would normally occur to one skilled in this art.

Figure 8:
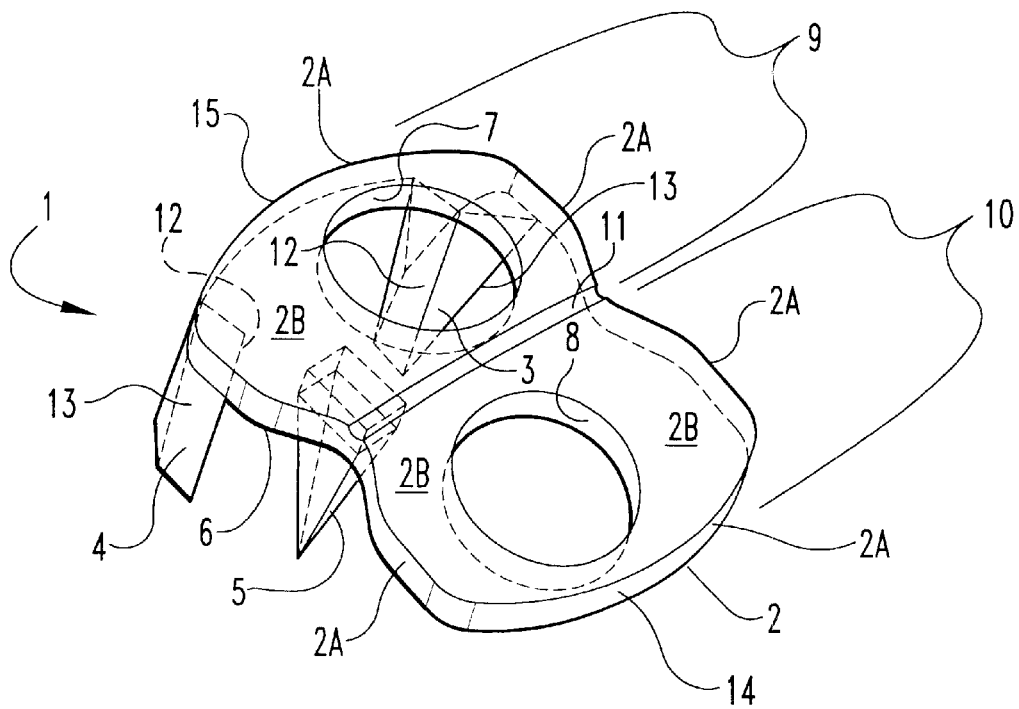
FIG. 8 is a perspective view of one embodiment of the present invention.

A spinal staple 1 according to the preferred embodiment of the present invention is depicted in FIG. 8. Staple 1 has a preferably bow-tie shaped body 2. The body 2 has a lateral edge 2A and an interior 2B. Body 2 can generally be subdivided in two halves by a groove 11. The first half 9 or wing 9 contains a hole 7 and the second half 10 or wing 10 contains a hole 8. Holes 7 and 8 can be either threaded or unthreaded. Three legs 3–5, prongs 3–5, or spikes 3–5 are attached to body 2 on the underside 6 of the first half 9. Legs 3 and 4 are unilateral with respect to body 2. Meaning, legs 3 and 4 are commonly attached near one end of the staple so that both legs 3 and 4 are more closely adjacent legged hole 7 than non-legged hole 8. Situated in this manner, legs 7 and 8 preferably attach toward the posterior side of the patient's vertebra, depending on the surgeon's installation. The third leg 5 is centrally mounted in the interior of body 2, preferably closer to legged hole 7 than non-legged hole 8, preferably on the same side of groove 11 as legs 3 and 4, and preferably not under groove 11. The inside edge 12 of legs 3 and 4 is preferably perpendicular to the underside 6. The outside edge 13 then tapers inwardly of the staple to intersect inside edge 12. The shape of leg 5 can be most anything that will work. In one embodiment, it is pyramidal and extends the same distance from underside 6 as legs 3 and 4.

Body 2 is preferably slightly convex in shape when viewed axially along groove 11, ends 14 and 15 being slightly bent or curved toward each other, generally at groove 11. The bow-tie shape and/or the presence of groove 11 in the present invention allows the surgeon to more easily bend and to conform staple 1 to complement the surface of the spine. The "pinched" middle resulting from the bow-tie shape and the presence of groove 11 reduce the amount of metal that the surgeon must deform to conform the staple to the patient's vertebra if compared to prior art devices. The reduced metal also affords increased visualization of the anatomy directly under the staple.

Figure 9:
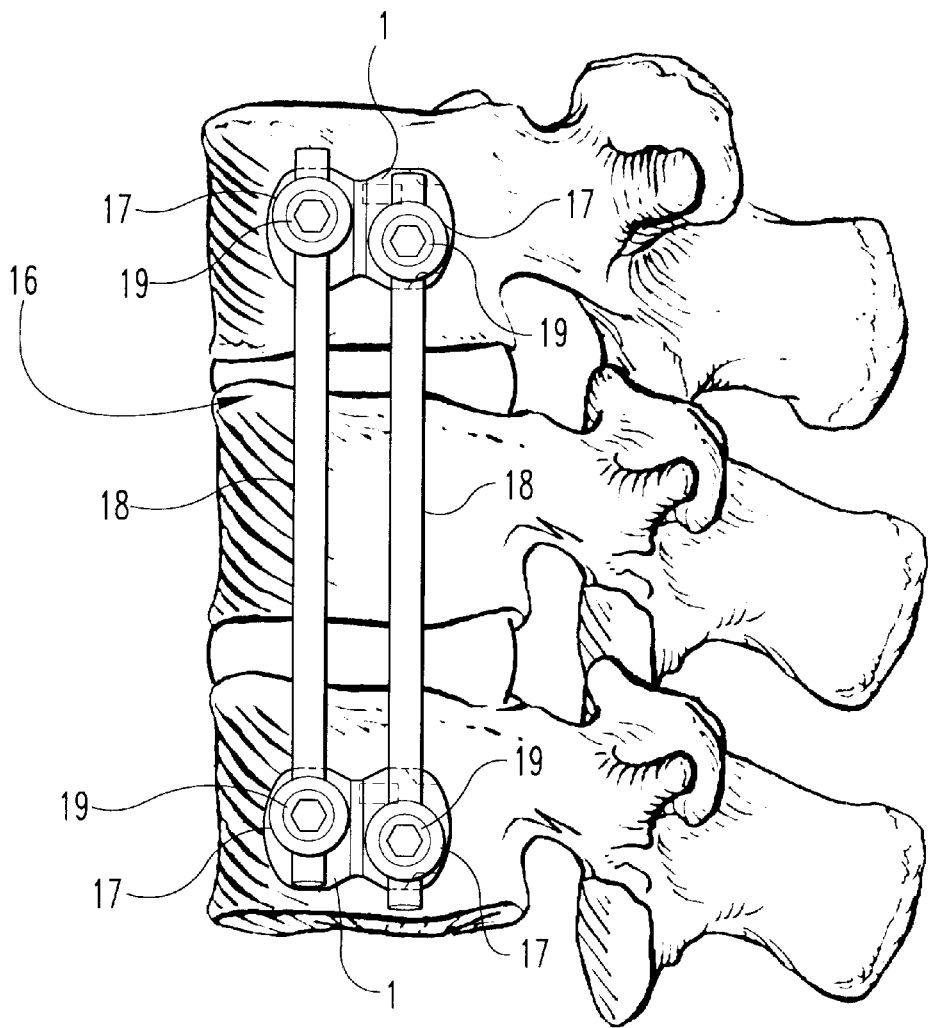
FIGS. 9, 10, and 11 are respectively front, top, and side views of spinal fixation systems that incorporate one embodiment of the present invention.
Figure 10:
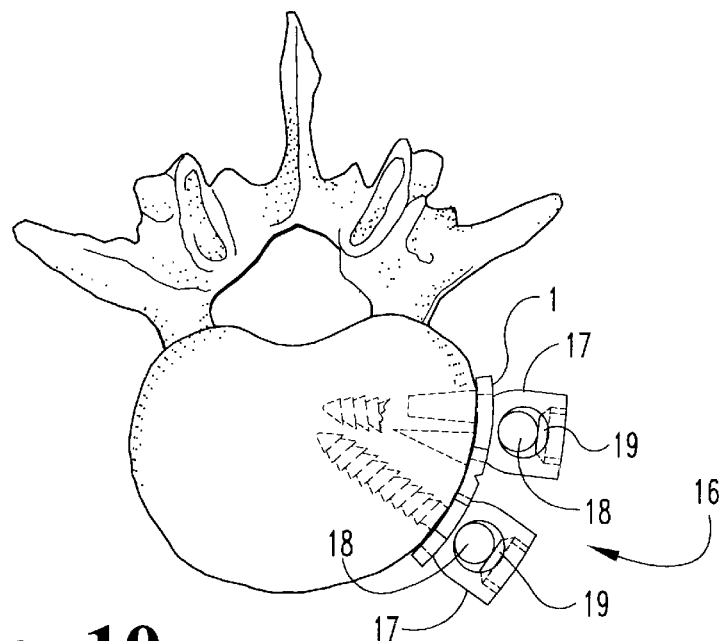
Figure 11:
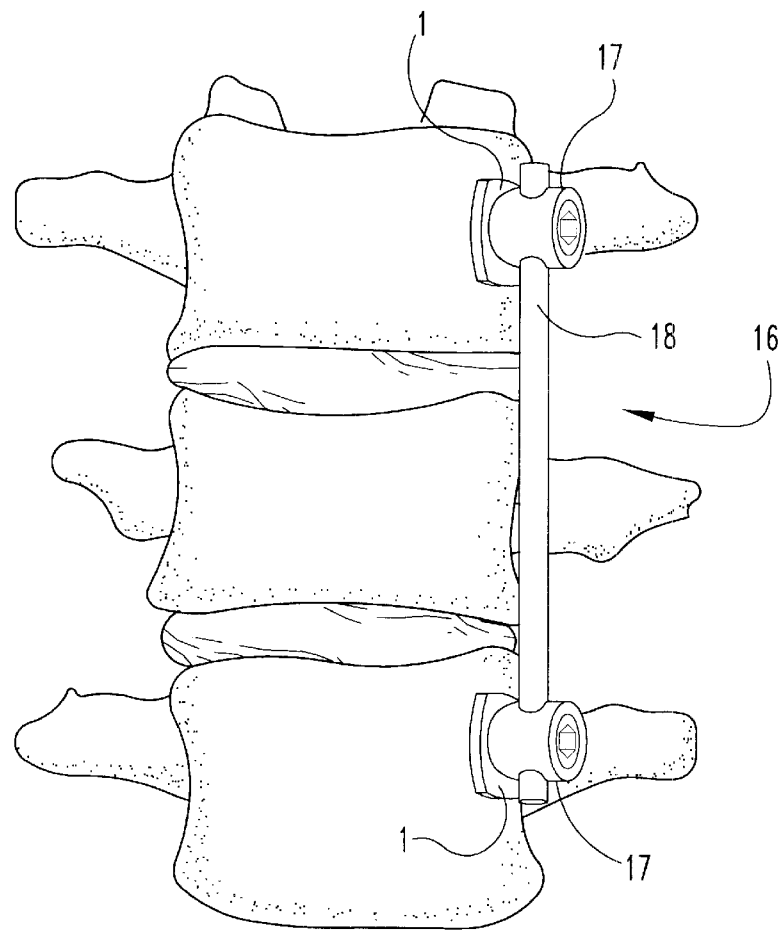

FIGS. 9–11 depict staple 1 in a spinal fixation system 16. System 16 has two vertebral staples, four vertebral bolts 17 or screws 17, two rods 18, and four clamps 19 or nuts 19 or plugs 19 to hold the rods 18 to screws 17. In this specification, the term "bolt" or "screw" refers to any various bone fasteners, including a standard bone screw, such as those sold under the trademark CD Horizon by Medtronic Sofamor Danek.

While the invention has been illustrated and described in detail and the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. By A spinal staple, comprising:
 a plate defining an outer edge extending about an interior region, said interior region defining first and second apertures therethrough;
 first and second legs extending from said plate adjacent said outer edge of said plate; and
 a third leg extending from said interior region of said plate between said first and second apertures and positioned intermediate said first and second legs.

2. The spinal staple of claim 1, wherein said first and second legs are positioned on a side of one of said first and second apertures opposite said third leg.

3. The spinal staple of claim 1, wherein said third leg is positioned closer to said one of said first and second apertures than the other of said first and second apertures.

4. The spinal staple of claim 1, wherein each of said first, second and third legs are positioned closer to one of said first and second apertures than the other of said first and second apertures.

5. The spinal staple of claim 1, wherein said third leg is centrally positioned between said first and second legs.

6. The spinal staple of claim 1, wherein said plate defines at least one groove extending laterally across said plate between said first and second apertures to facilitate bending of said plate.

7. The spinal staple of claim 1, wherein said plate defines at least one inwardly extending notch between said first and second apertures to facilitate bending of said plate.

8. The spinal staple of claim 1, wherein said plate defines an opposing pair of said inwardly extending notches to facilitate bending of said plate.

9. The spinal staple of claim 1, wherein each of said first and second apertures are threaded.

10. A spinal staple, comprising:
 a plate having a first end and an opposite second end, said plate defining a first aperture adjacent said first end and a second aperture adjacent said second end;
 a pair of outer prongs extending from said plate adjacent one of said first and second ends; and
 an inner prong extending from said plate between said first and second apertures and positioned intermediate said pair of outer prongs.

11. The spinal staple of claim 10, wherein said inner prong is positioned closer to one of said first and second apertures than the other of said first and second apertures.

12. The spinal staple of claim 10, wherein said pair of outer prongs each defines an outwardly facing surface extending contiguously from an outer edge of said plate.

13. The spinal staple of claim 10, wherein said pair of outer prongs define oppositely facing outer surfaces, said outer surfaces tapering inwardly toward one another to define an inwardly converging profile.

14. The spinal staple of claim 10, wherein said plate defines at least one groove extending laterally across said plate between said first and second apertures to facilitate bending of said plate.

15. The spinal staple of claim 10, wherein said plate defines at least one inwardly extending notch between said first and second apertures to facilitate bending of said plate.

16. The spinal staple of claim 15, wherein said plate defines an opposing pair of said inwardly extending notches between said first and second apertures to facilitate bending of said plate.

17. A spinal staple, comprising:
a plate including a first portion defining a first aperture and a second portion defining a second aperture, said first and second portions interconnected by a mid-portion having a reduced lateral width relative to said first and second portions to facilitate bending of said plate along said mid-portion; and
at least two prongs extending from said plate, one of said prongs positioned between said first and second apertures adjacent said mid-portion.

18. The spinal staple of claim 17, wherein said plate has an hour glass shape.

19. The spinal staple of claim 17, wherein said plate defines a groove extending laterally across said plate between said first and second apertures to facilitate bending of said plate along said mid-portion.

20. The spinal staple of claim 17, wherein said mid-portion is defined by at least one inwardly extending notch.

21. The spinal staple of claim 20, wherein said mid-portion is defined by an opposing pair of said inwardly extending notches.

22. The spinal staple of claim 17, wherein another of said prongs is positioned aside one of said first and second apertures opposite said mid-portion.

23. The spinal staple of claim 17, wherein a pair of said prongs is positioned aside one of said first and second apertures opposite said mid-portion, said one of said prongs positioned intermediate said pair of said prongs.

* * * * *

UNITED STATES PATENT AND TRADEMARK OFFICE
CERTIFICATE OF CORRECTION

PATENT NO.      : 6,533,787 B1
DATED           : March 18, 2003
INVENTOR(S)     : Lawrence G. Lenke et al.

It is certified that error appears in the above-identified patent and that said Letters Patent is hereby corrected as shown below:

Column 4,
Line 7, delete "By" before "A spinal staple, comprising:".

Signed and Sealed this

Second Day of September, 2003

JAMES E. ROGAN
*Director of the United States Patent and Trademark Office*